United States Patent [19]

Revis

[11] Patent Number: 4,746,750
[45] Date of Patent: May 24, 1988

[54] SYNTHESIS OF SILYL KETENE ACETAL FROM ALLYL 2-ORGANOACRYLATES

[75] Inventor: Anthony Revis, Freeland, Mich.

[73] Assignee: Dow Corning Corporation, Midland, Mich.

[21] Appl. No.: 91,166

[22] Filed: Aug. 31, 1987

[51] Int. Cl.$^4$ .............................. C07F 7/08; C07F 7/18
[52] U.S. Cl. .................................................... 556/443
[58] Field of Search ........................................ 556/443

[56] References Cited

U.S. PATENT DOCUMENTS

| | | | |
|---|---|---|---|
| 2,727,880 | 12/1955 | Hazelwood | 556/443 X |
| 3,529,007 | 9/1970 | Brison et al. | 556/443 |
| 3,607,902 | 9/1971 | Brison et al. | 556/443 |
| 4,414,372 | 11/1983 | Farnham et al. | 526/190 |
| 4,417,034 | 11/1983 | Webster | 526/190 |
| 4,482,729 | 11/1984 | Ishikawa | 556/446 |
| 4,508,880 | 4/1985 | Webster | 526/190 |

FOREIGN PATENT DOCUMENTS 0184692 6/1986 European Pat. Off. ...... 556/443 UX

OTHER PUBLICATIONS

Petrov et al., *J. Gen. Chem. (USSR)*, 29 (1959), pp. 2896–2899.
Ainsworth et al., *J. Organometallic Chem.*, 46 (1972), pp. 59–71.
Kita et al., *Tetrahedron Letters*, 24:12 (1983), pp. 1273–1276.
Brown, *J. Org. Chem.*, 39:9 (1974), pp. 1324–1325.
Kuo et al., *Chemical Communications*, (1971), pp. 136–137.
Ojima et al., *J. Organometallic Chem.*, 111 (1976), pp. 43–60.
Howe et al., *J. Organometallic Chem.*, 208 (1981), pp. 401–406.
Yoshii et al., *Chem. Pharm. Bull.*, 22 (1974), pp. 2767–2769.
Chen et al., *J. Am. Chem. Soc.*, 94:11 (1972), pp. 4037–4038.

*Primary Examiner*—Paul F. Shaver
*Attorney, Agent, or Firm*—Carl A. Yorimoto

[57] ABSTRACT

A process is described for preparing silyl ketene acetals having the formula, $$(CH_3)RC=C(OSiR^i{}_3)_2,$$

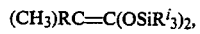

from allyl 2-organoacrylates. The process comprises contacting an allyl 2-organoacrylate with a trisubstituted silane in the presence of a rhodium catalyst; and separating and isolating the silyl ketene acetal. Silyl ketene acetal of greater than 85–90 percent purity can be recovered.

21 Claims, No Drawings

SYNTHESIS OF SILYL KETENE ACETAL FROM ALLYL 2-ORGANOACRYLATES

BACKGROUND OF THE INVENTION

This invention relates to a process for the manufacture of silyl ketene acetals. More specifically, this invention relates to a means for producing bis(silyl)ketene acetals (BSKA) having the formula, $$(CH_3)RC=C(OSiR^i{}_3)_2,$$

from the reaction of a trisubstituted silane and an allyl 2-organoacrylate having the formula, $$CH_2=CR\overset{\overset{O}{\|}}{C}OCH_2CH=CH_2.$$

R is selected from a group consisting of alkyl groups, aryl groups, alkaryl groups, and substituted alkyl, aryl, and alkaryl groups. $R^i$ is independently selected and is selected from a group consisting of alkyl groups, aryl groups, alkaryl groups, substituted alkyl, aryl, and alkaryl groups, alkoxy groups, halogen atoms, and organosiloxy groups.

The first reference to preparation of silyl ketene acetals (SKA) was in the late-1950's by Petrov et al., *J. Gen. Chem. (USSR)*, 29(1959), pp. 2896–2899. This reference and most of the other references to the art deal with chemical species of the general formula, $$R_3Si[\underset{\underset{Z}{|}}{O}C=C(CH_3)_2].$$
$$O(CH_2)_vZ$$

v has a value of 1 or more. Z is such groups as alkyl, alkenyl, aryl, alkaryl; any of these groups containing one or more functional groups, such as ether oxygen atoms, thio groups, organosiloxy groups, which are unreactive under silylating conditions.

Silyl ketene acetals are useful intermediates to prepare organic compounds which are difficult to synthesize by other means. Another recent application is the use of the SKA as acrylate polymerization initiators. This concept known as Group Transfer Polymerization (GTP) was developed by DuPont and is disclosed in three U.S. patents—U.S. Pat. No. 4,414,372, Farnham et al., issued Nov. 8, 1983; U.S. Pat. No. 4,417,034, Webster, issued Nov. 22, 1983; and U.S. Pat. No. 4,508,880, Webster, issued Apr. 2, 1985.

Four procedures for preparing silyl ketene acetals are known in the art. The first general route to SKA is the reaction of an ester of a carboxylic acid with an appropriate metal reagent to form a metal enolate ion and subsequent reaction of the enolate ion with an organochlorosilane. Ainsworth et al., *J. Organometallic Chem.*, 46 (1972), pp. 59–71, describe the preparation of an SKA via the reaction of esters of carboxylic acids with lithium diisopropylamide, followed by reaction with trimethylchlorosilane. Kita et al., *Tetrahedron Letters*, 24: 12 (1983), pp. 1273–1276, discloses a similar procedure to prepare bifunctional SKA. Brown, *J. Org. Chem.*, 39: 9 (1974), pp. 1324–1325, describes the preparation of metal enolate ions by reacting potassium hydride in tetrahydrofuran with a carbonyl compound, followed by reaction with excess triethylamine and trimethylchorosilane.

Kuo et al., *Chemical Communications*, (1971), pp. 136–137, discloses the preparation of bis(silyl)ketene acetals of the formula, $$R^1R^2C=C[OSi(CH_3)_3]_2,$$

wherein $R^1$ and $R^2$ are hydrogen, methyl, t-butyl, and phenyl. The silyl ketene acetal is prepared by the reaction of the corresponding carboxylic acid or silyl ester of a carboxylic acid in contact with lithium diisopropylamide, trimethylchlorosilane, and tetrahydrofuran.

In a second general procedure, silyl ketene acetals are prepared by the hydrosilation of esters of carboxylic acid with organohydrosilanes. Petrov et al., *J. Gen. Chem. (USSR)*, 29 (1959), pp. 2896–2899, described the platinum-catalyzed reaction of methyl methacrylate with triethylsilane. Ojima et al., *J. Organometallic Chem.*, 111 (1976), pp. 43–60, studied the use of tris(triphenylphosphine)rhodium chloride as a catalyst. Howe et al., *J. Organometallic Chem.*, 208 (1981), pp. 401–406, and Yoshii et al., *Chem. Pharm. Bull.*, 22 (1974), pp. 2767–2769, describe yields of 70–75% SKA from the reaction of $(C_2H_5)_3SiH$ and methyl methacrylate using organophosphorous complexes of rhodium as a catalyst. Quirk et al., in European Patent Application No. 0184692, published June 18, 1986, discloses o-silylated ketene acetals and enol ethers and a process for their preparation from the reaction of acrylate esters and silanes or siloxanes in the presence of a rhodium catalyst.

In a third procedure Ishikawa et al., U.S. Pat. No. 4,482,729, issued Nov. 13, 1984, describes the preparation of a fluoroalkyl silyl ketene acetal by the reaction of a fluorinated carboxylic acid ester with trimethylsilyl trifluoromethanesulfonate.

The fourth procedure involves the alkali metal reduction of disubstituted malonates in the presence of trimethylchlorosilane to produce a silyl ketene acetal. Kuo et al., *Chemical Communications*, (1971), pp. 136–137; and *J. Am. Chem. Soc.*, 94: 11 (1972), pp. 4037–4038, disclose the preparation of silyl ketene acetals of the formula, $$R^1R^2C=C(OR^3)OSi(CH_3)_3,$$

from the reaction of a dialkyl dialkylmalonate with trimethylchlorosilane in the presence of sodium metal. $R^1$, $R^2$, and $R^3$ are alkyl, aryl, or alkaryl groups.

It has now been discovered that bis(silyl)ketene acetals can be prepared by the reaction of a trisubstituted silane and an allyl 2-organoacrylate.

SUMMARY OF THE INVENTION

The instant invention is based upon the unexpected result that the hydrosilation reaction between an allyl 2-organoacrylate, $$CH_2=CR\overset{\overset{O}{\|}}{C}OCH_2CH=CH_2,$$

and a trisubstituted silane generates the BSKA, $$(CH_3)RC=C(OSiR^i{}_3)_2,$$

rather than the expected SKA, $$(CH_3)RC=C(OSiR^i_3)\!\!-\!\!OCH_2CH_2CH_2SiR^i_3.$$

The inventor of the instant invention believes that during the reaction of the allyl 2-organoacrylate with a trisubstituted silane the allylic group is liberated as propene.

The BSKA can be formed by the hydrosilation reaction of a tri(substituted)silyl 2-organoacrylate and a trisubstituted silane. However, the tri(substituted)silyl 2-organoacrylate, $$CH_2=CR\overset{O}{\overset{\|}{C}}OSiR^i_3,$$

is not a commercially available material and would require special synthesis for this reaction. Many allyl 2-organoacrylates, as for example allyl methacrylate, are commercially available materials. The ability to use an allyl 2-organoacrylate to produce a BSKA directly reduces the raw material and processing costs. The inventor of the instant invention further believes that a tri(substituted)silyl 2-organoacrylate is an intermediate formed during the reaction of an allyl 2-organoacrylate with a trisubstituted silane.

DESCRIPTION OF THE INVENTION

In accordance with the instant invention there is provided a process for the preparation of bis(silyl)ketene acetals from the reaction of a trisubstituted silane and an allyl 2-organoacrylate under conditions that will be delineated herein. What is described, therefore, is a process for preparing bis(silyl)ketene acetal having the formula, $$(CH_3)RC=C(OSiR^i_3)_2,$$

wherein, R is selected from a group consisting of alkyl groups, aryl groups, alkaryl groups, and substituted alkyl, aryl, and alkaryl groups; and each $R^i$ is independently selected from a group consisting of alkyl groups, aryl groups, alkaryl groups, substituted alkyl, aryl, and alkaryl groups, alkoxy groups, halogen atoms, and organosiloxy groups, said process comprising (A) contacting an allyl 2-organoacrylate having the formula, $$CH_2=CR\overset{O}{\overset{\|}{C}}OCH_2CH=CH_2,$$

wherein R is defined above, with a trisubstituted silane having the formula, $$R^i_3SiH,$$

wherein $R^i$ is defined above, in the presence of a rhodium catalyst; and (B) separating and isolating the bis(silyl)ketene acetal.

For the purposes of the instant invention, "substituted alkyl, aryl, and alkaryl groups" are alkyl, aryl, and alkaryl groups containing one or more functional substituents that are unreactive under silylating conditions. Examples of such functional groups are ether groups, tertiary amino groups, amido groups, thio groups, carbonyl groups, and organosiloxy groups. For the purposes of the instant invention, "organosiloxy groups" have the formula, $$—OSiR_3,$$

where R is defined, supra.

The BSKA prepared by the process of the instant invention can be, for example, $$(CH_3)_2C=C[OSi(CH_3)_3]_2,$$

$$(CH_3)(C_2H_5)C=C[OSi(CH_3)_3]_2,$$

$$(CH_3)_2C=C[OSi(CH_3)_2(C_2H_5)]_2,$$

$$(CH_3)(C_6H_5)C=C[OSi(CH_3)_3]_2,$$

$$(CH_3)(C_6H_4Cl)C=C[OSi(CH_3)_3]_2,$$

$$(CH_3)(CH_2Br)C=C[OSi(CH_3)_3]_2,$$

$$(CH_3)_2C=C[OSiCl_3]_2,$$

$$(CH_3)_2C=C[OSi(OCH_3)_3]_2,$$

$$(CH_3)_2C=C[OSi(CH_3)(C_6H_5)Cl]_2,$$

and $$(CH_3)_2C=C\{OSi[OSi(CH_3)_3]_3\}_2.$$

The allyl 2-organoacrylate may be, for example, $$CH_2=C(CH_3)\overset{O}{\overset{\|}{C}}OCH_2CH=CH_2 \text{ (allyl methacrylate),}$$

$$CH_2=C(C_2H_5)\overset{O}{\overset{\|}{C}}OCH_2CH=CH_2,$$

$$CH_2=C(C_3H_7)\overset{O}{\overset{\|}{C}}OCH_2CH=CH_2,$$

$$CH_2=C(C_4H_9)\overset{O}{\overset{\|}{C}}OCH_2CH=CH_2,$$

$$CH_2=C(C_6H_5)\overset{O}{\overset{\|}{C}}OCH_2CH=CH_2,$$

$$CH_2=C(C_6H_4Cl)\overset{O}{\overset{\|}{C}}OCH_2CH=CH_2, \text{ and}$$

$$CH_2=C(C_2H_4Br)\overset{O}{\overset{\|}{C}}OCH_2CH=CH_2.$$

The trisubstituted silane can be, for example—trimethylsilane, triethylsilane, dimethylethylsilane, i-propylmethylethylsilane, t-butyldimethylsilane, phenyldimethylsilane, trichlorosilane, trimethoxysilane, methylethylbromosilane, and tris(trimethylsilyloxy)silane.

Any rhodium catalyst known to catalyze hydrosilation reactions may be used in this invention. Examples of such catalysts are cited in the references of Ojima et al., Howe et al., Yoshii et al., and Quirk et al., supra. The preferred rhodium catalyst is selected from a group consisting of organorhodium complexes and rhodium catalysts with inorganic ligands. The organorhodium complexes can be, for example—tris(triphenylphosphine)rhodium chloride, $RhCl_3.(n-Bu_2S)_3$, or rhodium carbonyl chloride. The rhodium catalyst with inorganic ligands can be, for example—$RhCl_3.3H_2O$, $RhBr_3.3H_2O$, $Rh(NO_3)_3.xH_2O$, or $Rh_2(SO_4)_3.xH_2O$. Tris(triphenylphosphine)rhodium chloride and $RhCl_3.3H_2O$ are more preferred rhodium catalysts.

Concentrations of rhodium as low as 100 parts per million (ppm) on a molar basis relative to the allyl 2-organoacrylate are effective in facilitating the reaction of an allyl 2-alkylacrylate with a trisubstituted silane. However, reaction rates are proportional to catalyst concentration, and lower catalyst concentrations will result in proportionally lower reaction rates. Further, catalyst at concentrations of about 100 ppm can be easily rendered ineffective by small concentrations of impurities or other conditions that would inhibit the action of or poison the catalyst. Additionally, propene, a potential by-product of this reaction may form a complex with Group VIII metal catalysts. As such, the presence of propene may be a factor in inhibiting the effectiveness of the rhodium catalyst. A catalyst concentration in the range from about 500 to 2000 ppm rhodium on a molar basis relative to the allyl 2-organoacrylate is preferred to assure an effective level of catalyst to facilitate the reaction at a reasonable temperature and a reasonable reaction time. Levels of rhodium catalysts above 2000 ppm may yield some benefit in shortened reaction time. However, the cost of the additional catalyst may outweigh the benefit to be derived. As such, higher catalyst levels are possible but are not considered to offer further benefit.

The stoichiometric quantity of reactants to effect this reaction is 2.0 moles of the trisubstituted silane to each mole of the allyl 2-organoacrylate. To maximize the conversion of the 2-organoacrylate and the yield of the desired BSKA, the preferred mode of operation is addition of an excess of the trisubstituted silane. More preferably the trisubstituted silane should be present in the reaction mixture in a stoichiometric excess of at least 5 percent, a 2.1:1 molar ratio of the trisubstituted silane to the allyl 2-organoacrylate.

The reaction of the allyl 2-organoacrylate and the trisubstituted silane occurs at ambient temperatures. Preferably the reaction temperature should be greater than about 30° C. More preferably, the temperature during reaction of allyl 2-organoacrylate and the trisubstituted silane should be maintained in a range from about 30° to 80° C. The lower temperature is a minimum to assure that sufficient rate of reaction is achieved. The upper temperature is specified to minimize the polymerization of the allylic and vinylic functionalities of the allyl 2-organoacrylate. Such polymerization increases rapidly with increased temperature. Polymer formation detracts from the yield of the desired BSKA.

To minimize polymerization of the vinylic and allylic functionalities, a polymerization inhibitor may be optionally added. The polymerization inhibitor can be, for example, butylated hydroxytoluene (BHT or 2,6-di-t-butyl-4-methylphenol), hydroquinone, 4-methoxyphenol, or 4-methylphenol. Additionally, the polymerization inhibitor is made effective by the presence of oxygen. As such, the reaction could be run in an atmosphere of air. However, for safety's sake, it is preferred to purge the reactor system with an inert gas which has a low concentration of oxygen. Such an inert gas mixture, for example, could be a nitrogen purge which contains about 2 volume percent oxygen.

As discussed, supra, one of the potential intermediate products of this reaction is propene. To facilitate the progress of the reaction, the propene should be removed from the reaction zone. The pressure in the reaction zone during the reaction of the allyl 2-organoacrylate and the trisubstituted silane is preferably maintained at atmospheric pressure.

The allyl 2-organoacrylate and the trisubstituted silane are contacted in the presence of the rhodium catalyst at reaction conditions for a period of about 30 minutes or more. As demonstrated in the examples, infra, reaction times in a range of from about 30 to 180 minutes are adequate for completion of the reaction.

Silyl ketene acetal can be recovered by conventional means such as distillation. This is demonstrated in the example, infra. Conventional distillation column design can be specified to provide the capabilities to recover silyl ketene acetal at greater than 85 to 90 weight percent purity.

So those skilled in the art may better appreciate and understand the instant invention, the following examples are presented. These examples are presented to be illustrative and are not to be construed as limiting the claims delineated herein.

EXAMPLE 1

A solution of 25 g (0.2 mole) of allylmethacrylate (AMA), 4.3 ml of a 0.03M solution of $RhCl_3.3H_2O$ in tetrahydrofuran (THF), and 0.32 g of butylated hydroxytoluene (BHT), a polymerization inhibitor, were charged to a laboratory reaction flask. The rhodium content of the above mixture was approximately 500 ppm on a molar basis relative to the AMA. The reaction flask was fitted with a mechanical agitator, provisions for heating, and a reflux condenser. The flask was purged with nitrogen gas which contained 2 volume percent oxygen.

The contents of the flask were heated to 41° C. Trimethylsilane (TMS) was fed to the flask as a liquefied gas under pressure. When a few ml of TMS were added to the flask, the temperature of the contents of the flask heated to 65° C. The heating mantle was lowered and the contents of the flask cooled to 54° C. Approximately 10-15 ml of TMS was then added to the flask. The contents of the flask then cooled to 31° C. without evidence of reaction. 2 ml of the 0.03M solution of $RhCl_3.3H_2O$ in THF was added to the flask. No noticeable exotherm was observed. The reaction mixture was again heated. At 65° C. 4 ml of the THF/rhodium catalyst solution was added to the flask. Addition of TMS was resumed. The temperature of the reaction mixture rose to 77° C. The alternate cooling of the reaction flask and addition of TMS continued until the analysis of the mixture showed total consumption of the AMA, a total of about 61 ml (0.52 mole) of TMS had been added. The final rhodium content of the mixture in the flask is approximately 1200 ppm on a molar basis relative to the AMA.

Samples of the contents of the flask were taken at 51, 64, 78, and 115 minutes after the start of the first addition of TMS. These samples are designated as Samples A, B, C, and D, respectively. These samples were analyzed by gas chromatography and mass spectroscopy. These analytical techniques identified the silyl ketene acetal,

a component which is a mixture of unreacted AMA and trimethylsilylmethacrylate (TMSMA),

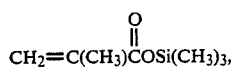

and the catalyst solvent, THF. A mass spectroscopic-gas chromatographic technique showed that the contents of the flask contained none of the carbonyl adduct,

Table 1 is a summary of the results of analyses. The results presented are the content of THF, designated "%THF"; the mixture of the unreacted AMA and the TMSMA, designated as "%Mix"; the BSKA content, designated as "%SKA"; and remainder of the contents, designated as "%Other"; the results being reported in gas chromatography area percent.

TABLE 1

| Sample | % THF | % Mix | % SKA | % Other |
|---|---|---|---|---|
| A | 15.1 | 60.7 | 2.0 | 21.2 |
| B | 11.1 | 27.5 | 29.1 | 32.9 |
| C | 14.7 | 30.9 | 23.6 | 20.8 |
| D | 15.7 | 4.6 | 56.4 | 23.2 |

The above results demonstrate the unexpected formation of a bis(silyl)ketene acetal rather than the expected formation of a silyl ketene acetal having the formula,

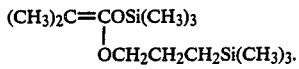

EXAMPLE 2

Similar raw materials, equipment, procedures, and analyses as utilized in Example 1 were applied. A solution of 126 gm (1.0 mole) of AMA, 29 ml of a 0.03M solution of RhCl$_3$.3H$_2$O in THF, and 0.13 gm of BHT were added to a flask and agitated rapidly. The flask and its contents were purged with a nitrogen stream that contained 2 volume percent oxygen.

The procedure of small additions of TMS, followed by cooling to absorb the exotherm, followed by subsequent additions of TMS, and additions of the rhodium catalyst solution, as needed, was followed.

Table 2 is a summary of the addition of TMS and the rhodium catalyst solution to the flask as a function of time. Table 2 also lists the time at which samples were taken. The running time in minutes from the start of the run is designated in Table 2 as "Time"; the amount of TMS in milliliters is designated "ml TMS"; the amount of the rhodium catalyst solution is designated by "ml Cat"; and the sample taken from analyses are designated by "Sample" and identified by letter, beginning with E.

TABLE 2

| Time | ml TMS | ml Cat | Sample |
|---|---|---|---|
| 0 | 0 | 29 | — |
| 7 | 40 | — | — |
| 10 | 25 | — | E |
| 27 | 16 | — | — |
| 32 | 40 | — | — |
| 38 | 60 | — | F |
| 47 | — | 7 | — |
| 57 | 60 | 15 | — |
| 62 | — | 10 | G |
| 72 | — | 10 | — |
| 78 | 60 | 10 | — |

TABLE 2-continued

| Time | ml TMS | ml Cat | Sample |
|---|---|---|---|
| 91 | — | — | H |

Thus a total of 300 ml (2.6 mole) of TMS was added. A total of 52 ml (approximately 1800 ppm Rh on a molar basis relative to the starting AMA) was added before and during the feeding of TMS. The temperature of the mixture in the flask varied from 42° to 101° C. Approximately 290 g of crude product was contained in the flask.

Samples E, F, G, and H, respectively were analyzed by gas chromatography and mass spectroscopy. Table 3 is a summary of these analyses. The notation in Table 1 will be utilized.

TABLE 3

| Sample | % THF | % Mix | % SKA | % Other |
|---|---|---|---|---|
| E | 11.5 | 78.9 | — | 9.6 |
| F | 9.9 | 53.6 | 8.1 | 29.5 |
| G | 19.9 | 12.1 | 37.9 | 30.1 |
| H | 22.2 | 5.4 | 41.5 | 30.9 |

No evidence of the carbonyl adduct (CA) was detected.

The crude product was placed in a laboratory rotary evaporator to remove low-boiling materials. The crude product, stripped of low-boiling materials had an SKA content of 68.5 percent. The crude product was then distilled in a laboratory distillation column, 3 feet long and 1 inch in diameter. The distillation column was packed with ceramic saddles. Distillation was carried out at a pressure of 15 mm Hg. Product cuts were made at an overhead temperature of 71° C. Five product cuts, totalling 88 g, were taken. The SKA content of these cuts ranged from 86.6 to 92.3 percent. No evidence of CA was detected.

The above results demonstrate the preparation and recovery of a bis(silyl)ketene acetal, BSKA, from the reaction of a trisubstituted silane with an allyl 2-organoacrylate in the presence of a rhodium catalyst.

EXAMPLE 3

The equipment, procedures, and analyses utilized in Example 2 were used. The same raw materials were used with the exception that tris(triphenylphosphine)rhodium chloride was used as the catalyst. The final reaction mixture was formed from the overall addition of 170 ml (108.5 g or 1.47 mole) of TMS to 63 g (0.5 mole) of AMA in the presence of 0.77 g (8.3×10$^{-4}$ moles) of tris(triphenylphosphine)rhodium chloride. The rhodium content of the final mixture was approximately 1600 ppm on a molar basis relative to the AMA.

The additions of TMS and the rhodium catalyst were accomplished over a period of time of 105 minutes. The temperature of contents of the flask ranged from 39° to 104° C. Periodic samples were taken during the course of the run for analyses to track the progress of the run. The final analysis showed that the crude product had no AMA and an SKA content of 52.2 percent. There was no evidence of the presence of CA.

The results show that an organorhodium complex is an effective catalyst for the reaction of a trisubstituted silane and an allyl 2-organoacrylate to form a bis(silyl)ketene acetal.

What is claimed is:

1. A process for preparing bis(silyl)ketene acetal having the formula, $(CH_3)RC=C(OSiR^i_3)_2$, wherein, R is selected from a group consisting of alkyl groups, aryl groups, alkaryl groups, and substituted alkyl, aryl, and alkaryl groups; and each $R^i$ is independently selected from a group consisting of alkyl groups, aryl groups, alkaryl groups, substituted alkyl, aryl, and alkaryl groups, alkoxy groups, halogen atoms, and organosiloxy groups, said process comprising (A) contacting an allyl 2-organoacrylate having the formula, $$CH_2=CRCOCH_2CH=CH_2,$$
(with O double-bonded to C)

wherein R is defined above, with a trisubstituted silane having the formula, $R^i_3SiH$, wherein $R^i$ is defined above, in the presence of a rhodium catalyst; and (B) separating and isolating the bis(silyl)ketene acetal.

2. A process according to claim 1, wherein the rhodium catalyst is selected from a group consisting of organorhodium complexes and rhodium catalysts with inorganic ligands.

3. A process according to claim 2, wherein the organorhodium complex is tris(triphenylphosphine)rhodium chloride.

4. A process according to claim 2, wherein rhodium catalyst with inorganic ligands is $RhCl_3 \cdot 3H_2O$.

5. A process according to claim 1, wherein the rhodium concentration relative to the allyl 2-organoacrylate is at least 100 parts per million on a molar basis.

6. A process according to claim 1, wherein the trisubstituted silane is present in a stoichiometric excess greater than about 5 percent relative to the allyl 2-organoacrylate.

7. A process according to claim 1, wherein the reaction temperature is greater than about 30° C.

8. A process according to claim 1, wherein reaction between the allyl 2-organoacrylate and the trisubstituted silane is allowed to proceed for at least 30 minutes.

9. A process according to claim 1, wherein distillation is used to separate and isolate the bis(silyl)ketene acetal.

10. A process according to claim 1, wherein the allyl 2-organoacrylate compound is allyl methacrylate, the trisubstituted silane is $(CH_3)_3SiH$, the rhodium concentration is greater than 100 parts per million on a molar basis relative to the allyl 2-organoacrylate, the reaction temperature is greater than about 30° C., the reaction time is at least 30 minutes, and the bis(silyl)ketene acetal, $(CH_3)_2C=C[OSi(CH_3)_3]_2$, is separated and isolated by distillation.

11. A process according to claim 10, wherein the rhodium concentration is in a range from about 500 to 2000 ppm, the reaction temperature is in a range from about 30° to 80° C., the reaction time is in a range from about 30 to 180 minutes, and the bis(silyl)ketene acetal is recovered at a purity of greater than about 85 weight percent.

12. A process according to claim 1, wherein the bis(silyl)ketene acetal is $(CH_3)_2C=C[OSi(CH_3)_3]_2$.

13. A process according to claim 1, wherein the bis(silyl)ketene acetal is $(CH_3)(C_2H_5)C=C[OSi(CH_3)_3]_2$.

14. A process according to claim 1, wherein the bis(silyl)ketene acetal is $(CH_3)_2C=C[OSi(CH_3)_2(C_2H_5)]_2$.

15. A process according to claim 1, wherein the bis(silyl)ketene acetal is $(CH_3)(C_6H_5)C=C[OSi(CH_3)_3]_2$.

16. A process according to claim 1, wherein the bis(silyl)ketene acetal is $(CH_3)(C_6H_4Cl)C=C[OSi(CH_3)_3]_2$.

17. A process according to claim 1, wherein the bis(silyl)ketene acetal is $(CH_3)(CH_2Br)C=C[OSi(CH_3)_3]_2$.

18. A process according to claim 1, wherein the bis(silyl)ketene acetal is $(CH_3)_2C=C[OSiCl_3]_2$.

19. A process according to claim 1, wherein the bis(silyl)ketene acetal is $(CH_3)_2C=C[OSi(OCH_3)_3]_2$.

20. A process according to claim 1, wherein the bis(silyl)ketene acetal is $(CH_3)_2C=C[OSi(CH_3)(C_6H_5)Cl]_2$.

21. A process according to claim 1, wherein the bis(silyl)ketene acetal is $(CH_3)_2C=C\{OSi[OSi(CH_3)_3]_3\}_2$.

* * * * *